(12) United States Patent
Abraham et al.

(10) Patent No.: US 11,645,746 B2
(45) Date of Patent: May 9, 2023

(54) DENTAL IMAGE SEGMENTATION AND REGISTRATION WITH MACHINE LEARNING

(71) Applicant: Orca Dental AI Ltd., Herzeliya (IL)

(72) Inventors: Zeev Abraham, Herzeliya (IL); Daniel Abraham, Raanana (IL); Shlomo Avigdor, Kfar-Yona (IL)

(73) Assignee: Orca Dental AI LTD., Herzeliya (IL)

( * ) Notice: Subject to any disclaimer, the term of this patent is extended or adjusted under 35 U.S.C. 154(b) by 0 days.

(21) Appl. No.: 16/699,296

(22) Filed: Nov. 29, 2019

(65) Prior Publication Data

US 2020/0175678 A1 Jun. 4, 2020

Related U.S. Application Data

(60) Provisional application No. 62/772,419, filed on Nov. 28, 2018.

(51) Int. Cl.
*G06T 7/00* (2017.01)
*G06T 7/11* (2017.01)
*G16H 30/40* (2018.01)

(52) U.S. Cl.
CPC ............ *G06T 7/0012* (2013.01); *G06T 7/11* (2017.01); *G16H 30/40* (2018.01); *G06T 2200/04* (2013.01); *G06T 2200/08* (2013.01); *G06T 2207/10072* (2013.01); *G06T 2207/20084* (2013.01); *G06T 2207/30036* (2013.01)

(58) Field of Classification Search
CPC ............ G06T 7/11; G06T 2207/30036; G06T 7/0012; G06T 2200/04; G06T 2200/08; G06T 2207/10072; G06T 2207/20084; G06T 2207/10081; G06T 2207/20081; G16H 30/40; G16H 50/20
See application file for complete search history.

(56) References Cited

U.S. PATENT DOCUMENTS

2019/0148005 A1* 5/2019 Domracheva .......... G06K 9/342
 345/424
2020/0320685 A1* 10/2020 Anssari Moin ....... G06T 11/008

OTHER PUBLICATIONS

Miki et al. "Tooth Labelling in Cone-Beam CT Using Deep Convolutional Neural Network for Forensic Identification." SPIE Medical Imaging, Mar. 3, 2017, 7 pages (Year: 2017).*

* cited by examiner

Primary Examiner — Jon Chang
(74) Attorney, Agent, or Firm — Intrinsic Law Corp.

(57) ABSTRACT

A system and method are disclosed for representing and studying anatomy in the oral region such as parts of a subject's teeth and adjoining tissues. Types of inputs are used to form segmented outputs representing the teeth and can include segmented crown and root portions of the teeth. Machine learning methods are used for optimum and accurate results and to generate data objects corresponding to respective anatomical features of the subject.

9 Claims, 16 Drawing Sheets

24

DENTAL IMAGE SEGMENTATION AND REGISTRATION WITH MACHINE LEARNING

CROSS-REFERENCE TO RELATED APPLICATIONS

This application claims the benefit and priority of U.S. Provisional patent application Ser. No. 62/772,419 filed Nov. 29, 2018, entitled DENTAL SEGMENTATION AND REGISTRATION WITH MACHINE LEARNING, which is hereby incorporated by reference.

TECHNICAL FIELD

The present application is related to imaging of dental and related anatomy, including generating and processing of images and data for the same.

BACKGROUND

Systems for imaging dental anatomy (generally in the region of the teeth, jaws, mouth and proximal areas of the head or maxillofacial region) are known but have a number of limitations addressed herein. While x-ray imaging and/or computed tomography (CT) imaging are acceptable for many diagnostic and clinical purposes, a need remains for high-accuracy multi-component imaging of the teeth and related structures. One method of imaging a patient's dental region is using a dental cone beam CT (CBCT), which can be used to generate multi-dimensional images (e.g., 3-dimensional or 3D images) of the region. FIG. 1 illustrates an exemplary computer-generated image output 10 resulting from a prior art CBCT scan.

In CBCT a special x-ray machine connected to a computer processor and control system rotates a conical beam source and a detector about the subject's head to generate a plurality of images in a corresponding plurality of planes or slices through the subject. The resulting data is reconstructed by a computer running a special computer program and is compiled into an image file providing a flat 3D representation of the patient's dental anatomy by way of a special file viewer. However, such systems can only provide flattened image files for display on traditional computer displays and printing devices, which can further be filtered using substantially conventional image filtering and image processing techniques, for example to enhance a type of region or pixel, or to adjust the image contrast, saturation or other processing of the entire image field.

Other methods of generating 3D dental images include intra-oral optical scanning and scanning of a mechanical mold taken from the mouth of a subject. Again, the 3D aspect of these outputs are limited and treat an entire image field without discrimination to anatomical knowledge regarding the image. The three-dimensionality of such prior methods and systems is limited to their ability to offer a scene view of some region of interest and sometimes selectably rotate the view so that the viewing user could appreciate the scene from the new angle or perspective. The prior art, even if it were able to identify or segment a portion of an image at all (which it generally cannot) would at most be able to highlight or encircle or similarly annotate a region of interest and is based on filtering of graphical images and related techniques only.

Partly on account of their limited discrimination and inability to process various radiodensities and dynamic range limitations, presently available methods lack the clarity, resolution or ability to accurately and automatically distinguish or segment individual anatomical features of the 3D image. Features that dental practitioners may wish to segment for further examination include individual teeth, roots, crowns, maxillae, mandibles, nerve canals or other anatomical features. Automated segmentation of such features cannot be performed with present methods, so that manual segmentation by skilled operators is required.

For example, U.S. Pat. No. 10,049,457, incorporated herein by reference, discusses a system and method for automating analysis of cephalometric x-rays, including automatic localization of anatomical landmarks using convolutional neural networks. This and other techniques have allowed useful identification of one or more landmarks in dental images, but lack true anatomical associations of organs, bones, teeth, nerves or similar parts of the human body under observation.

There therefore exists a need for an automated system which can accurately segment anatomical features of a 3D image and present each segmented anatomical feature or combination of features as an individual data file corresponding to a 3D segmented image which may be viewed with an imaging device. It would be advantageous for treatment planning and follow-up if a dental practitioner had the ability to view an image of an individual feature, such as a single tooth, and to manipulate that image, in isolation or with respect to images of other anatomical features.

SUMMARY

To address the need for accurate segmentation of anatomical features of a 3D image for the purpose of treatment planning and follow-up, the present disclosure is directed to methods for segmenting features of a 3D image using machine learning steps. In an aspect of the present disclosure, the machine learning steps employ convolutional neural networks (CNN).

An aspect and embodiment is directed to a method for automated processing of a 3D image in a processor-based machine, the method comprising receiving the 3D image, performing a sequence of automated segmentation of anatomical features of the received dental image to produce segmented anatomical features, the segmentation based on machine learning from previously-analyzed dental images, creating a segmented data file corresponding to one or more of the segmented anatomical features, formatting the segmented data file so that the one or more segmented anatomical features are viewable by a user on a display device, and providing the segmented data file to the user.

An aspect and embodiment is directed to a system for digitally segmenting representations of a patient's anatomy based on medical images thereof, comprising a medical image processor configured and arranged to receive and transform three-dimensional (3D) image data from a medical imaging device; a machine learning processor configured and arranged to receive and transform stored data from a database, the stored data comprising historical data of a plurality of anatomy, not of said patient, said machine learning processor further configured and arranged to automatically determine one or more attributes of said 3D image data based on said stored data; a segmentation processor configured and arranged to output a segmented 3D data object corresponding to said patient's anatomy An aspect and embodiment is directed to a method for presenting and processing medical image data and corresponding data objects, comprising in a medical image processor, receiving one or more three-dimensional (3D)

images of at least an anatomical object; in a machine learning processor, receiving a plurality of stored data from a coupled data store, and processing said stored data as well as said 3D images to determine one or more attributes of said 3D image data based on said stored data; and in a segmentation processor, generating and outputting a segmented 3D data object corresponding to said anatomical object.

IN THE DRAWINGS

For a fuller understanding of the nature and advantages of the present technology, reference is made to the following detailed description of preferred embodiments and in connection with the accompanying drawings, in which.

DETAILED DESCRIPTION

Figure 1:
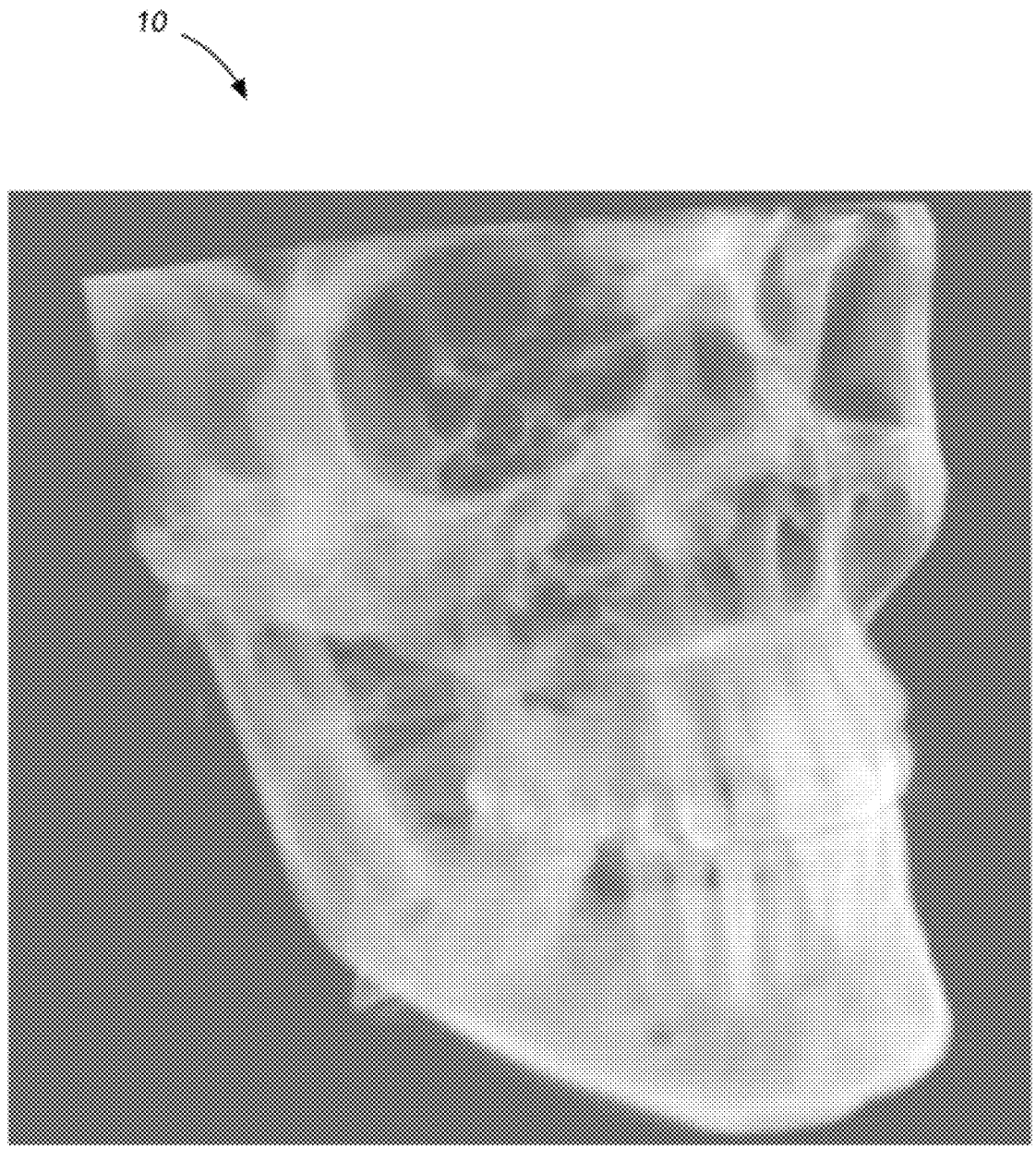
FIG. 1 illustrates a computer-generated CBCT image according to the prior art.

The present invention encompasses systems, methods, data structures, computer or machine-readable instruction sets, output data structures configured and adapted for generating digital data and/or images. Additionally, architectures employing the foregoing can be implemented in stand-alone computing machines or clients, network-connected servers, cloud-based computers and data stores, or combinations thereof.

While some parts of the system described are implemented using components available (such as devices used in imaging, communication, data processing, storage and so on) these components may be used in new and novel ways according to the invention, and may further be modified and adapted for use in or with the present system and method. Specifically, as will be discussed, various image and/or data gathering and processing circuits, and other features and components of the invention are designed, connected, programmed or executed in special and new ways to achieve the present objectives and attain the described outcomes and results, which a conventional system was never configured or arranged to do. In so doing, the present system and method significantly improve on the design and functioning of said system or components of the system (and the resulting method carried out thereby).

As an example, new and technologically-useful data objects, structures, tables, signals or other electronic elements that represent and convey novel and useful information have been devised and are input into, processed by, and output from components of the present system in the course of carrying out the present method. Newly generated data objects or files indicate or signal or represent and facilitate clinical conditions and are used to achieve and cause electronic processors, displays, imagers and other diagnostic and/or therapeutic systems to operate according to the present teachings. In some regards, these new data objects enable human practitioners to interactively observe, diagnose, study and manipulate what is needed to form clinical outcomes in the treatment of patient dental conditions technically differently from previous dental imaging or image processing systems and methods. An actual three-dimensional representation and identifying data object can be generated following the present teachings for a physical anatomy of interest so that the data object is essentially a realistic representation of the physical anatomy of interest. Computer-based interactions between a machine and/or human operator and the new data objects of the invention enables novel results that include the output and creation of new and useful imagery, simulations based on real knowledge, and other data and information creation and output to tangibly affect the clinical environment in which a patient and a practitioner are active.

No method or system was previously configured to take in signals and data files representing dental (or other medical) imagery and operate on the same using a programmable circuit or processor, and further using a machine learning engine and connected data store, in order to define a physical analog of an anatomical part of the body and extract and segment and register said body part or anatomy, and generate an equivalent electronic data object corresponding thereto which can then be stored, processed, shared, and manipulated using man-machine interfaces (like a user interface) so as to manipulate fairly directly the data object in question. By taking existing and new components, instructions, processors executing said instructions, and computer-based input and output modules the present inventors have conceived of and implemented such a new and useful system and method for the first time.

In an aspect, the present system and method employ both CT input data as well as intra-oral data or denture model scan data (referred to as intra-oral scan or "IOS"). In another aspect, the CT and IOS data are combined to provide a more useful data or image outputs and results usable by practitioners in diagnosing, treating or studying human or animal subjects. In yet another aspect, the present system and method are configured to indicate, identify and accurately segment various parts of the dental anatomy, including the teeth, roots, jaw bones, crowns, and surrounding tissue. In still another aspect, the invention employs machine learning, artificial intelligence, neural network learning techniques and other advanced methods to more accurately achieve the foregoing and to provide a level of data and image output previously not achievable with conventional technology.

As stated earlier, CBCT images can provide a data set on which computers and computer-implemented methods can operate. In the present context, the inventors have developed segmentation methods to extract desired portions of an image (or data set) from a larger data set, e.g., a CBCT data set. Specifically, the teeth, mandible (lower jaw), maxilla (upper jaw), soft tissues or other anatomical features of a subject may be segmented out of such a data set.

Figure 2A:
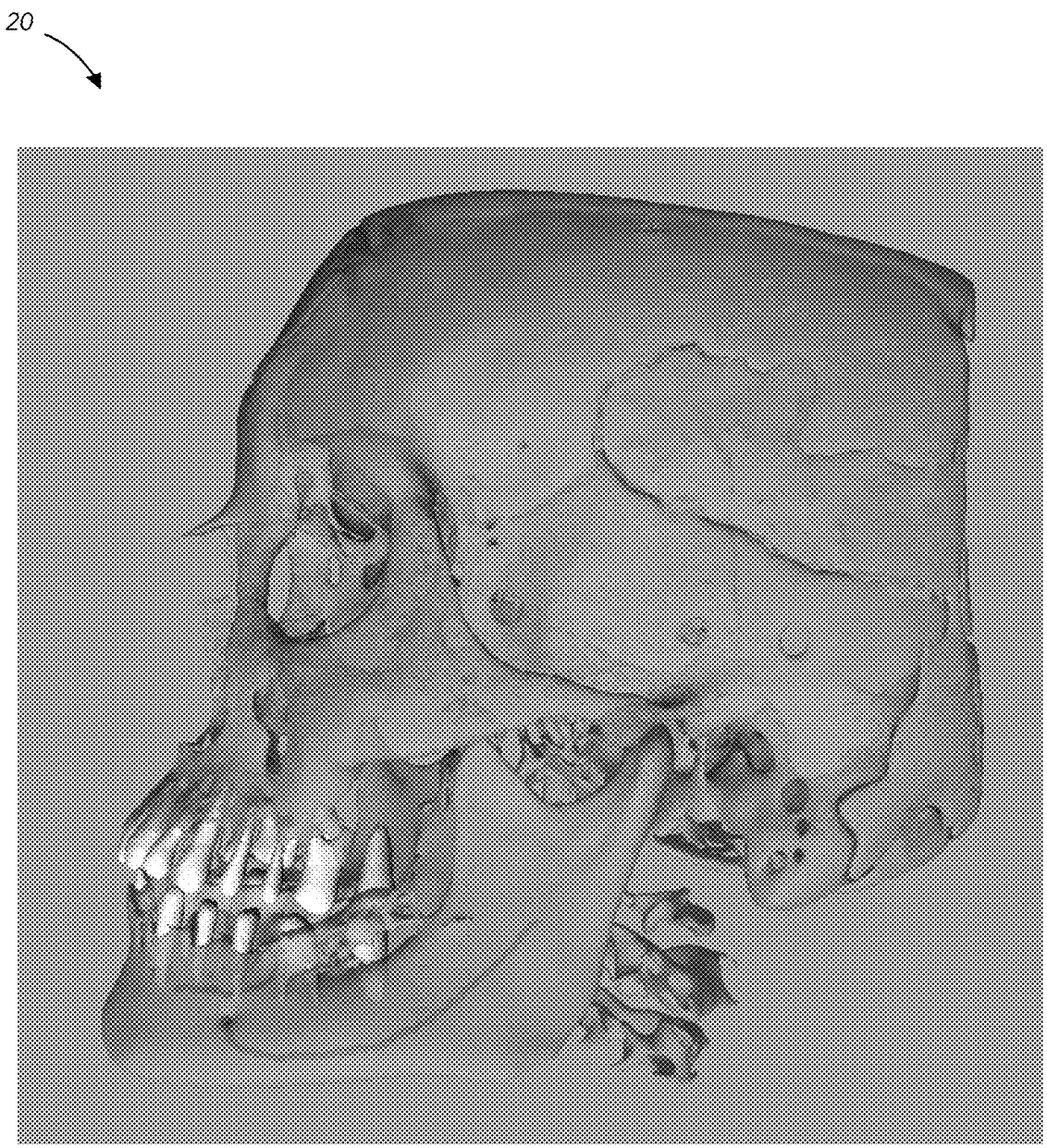
FIGS. 2A, 2B and 2C illustrate segmentation of anatomical features of a subject from an exemplary CBCT data set.
Figure 2B:
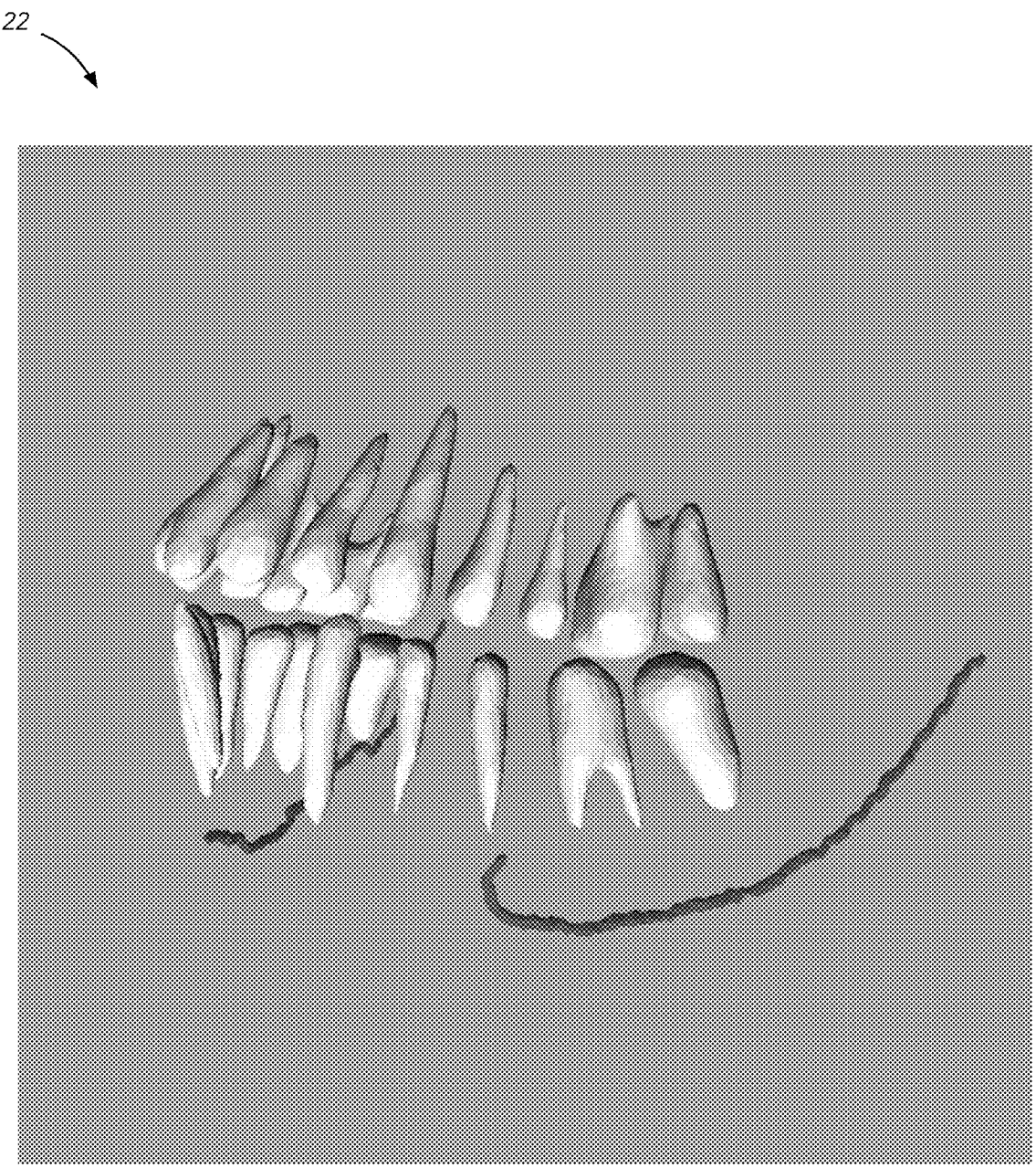
Figure 2C:
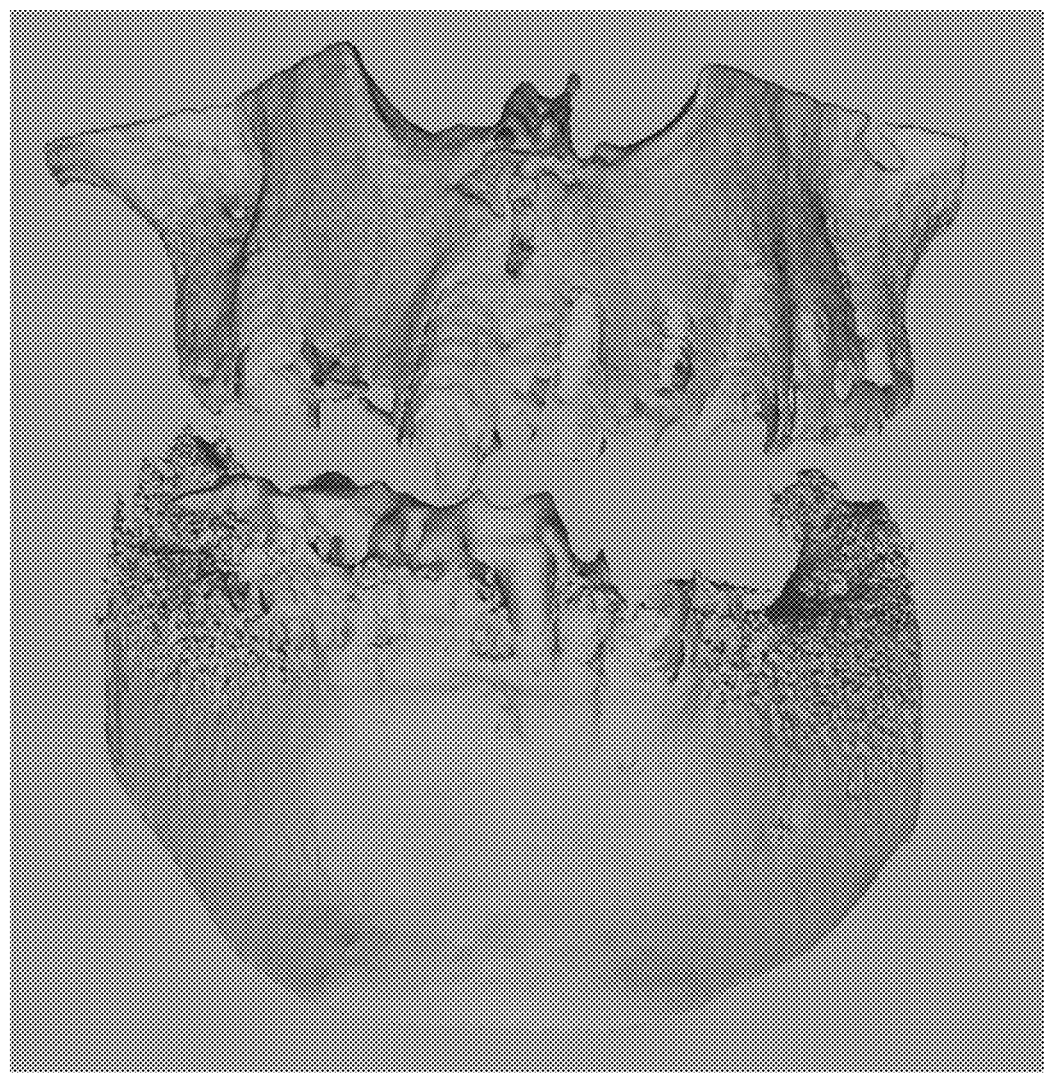

FIGS. 2A, 2B and 2C illustrate segmentation of anatomical features from a CBCT data set. FIG. 2A shows the complete CBCT data set 20, with the teeth highlighted showing that their location has been detected and segmented by the present system and method. FIG. 2B is a representation 22 of the teeth shown removed from the other anatomical features, and FIG. 2C is a representation 24 of the bony structures of CBCT data set 20 with the teeth removed.

As mentioned above and to be explained further herein, we see that the invention comprises hardware and/or software that is specially purposed and arranged to directly identify, isolate or segment and provide for processing a newly-identified and generated data object corresponding to one or more anatomical objects found in the patient imagery. As seen, the distinct anatomy such as the patient's teeth (all, or any one or plurality of said teeth) can be selectively identified using the present machine-assisted techniques in a way that no human operator could hope to accomplish. Once the anatomy of interest is identified (for example the teeth) using the present methods, individual machine-readable output files, tables, images or other data objects corresponding thereto can be processed for saving, displaying or operating thereon. As will be explained further, a user interface tool in a computer can be employed to then interactively present the output data object to a clinical user, patient or other party needing to study the isolated anatomical object(s).

Figure 3A:
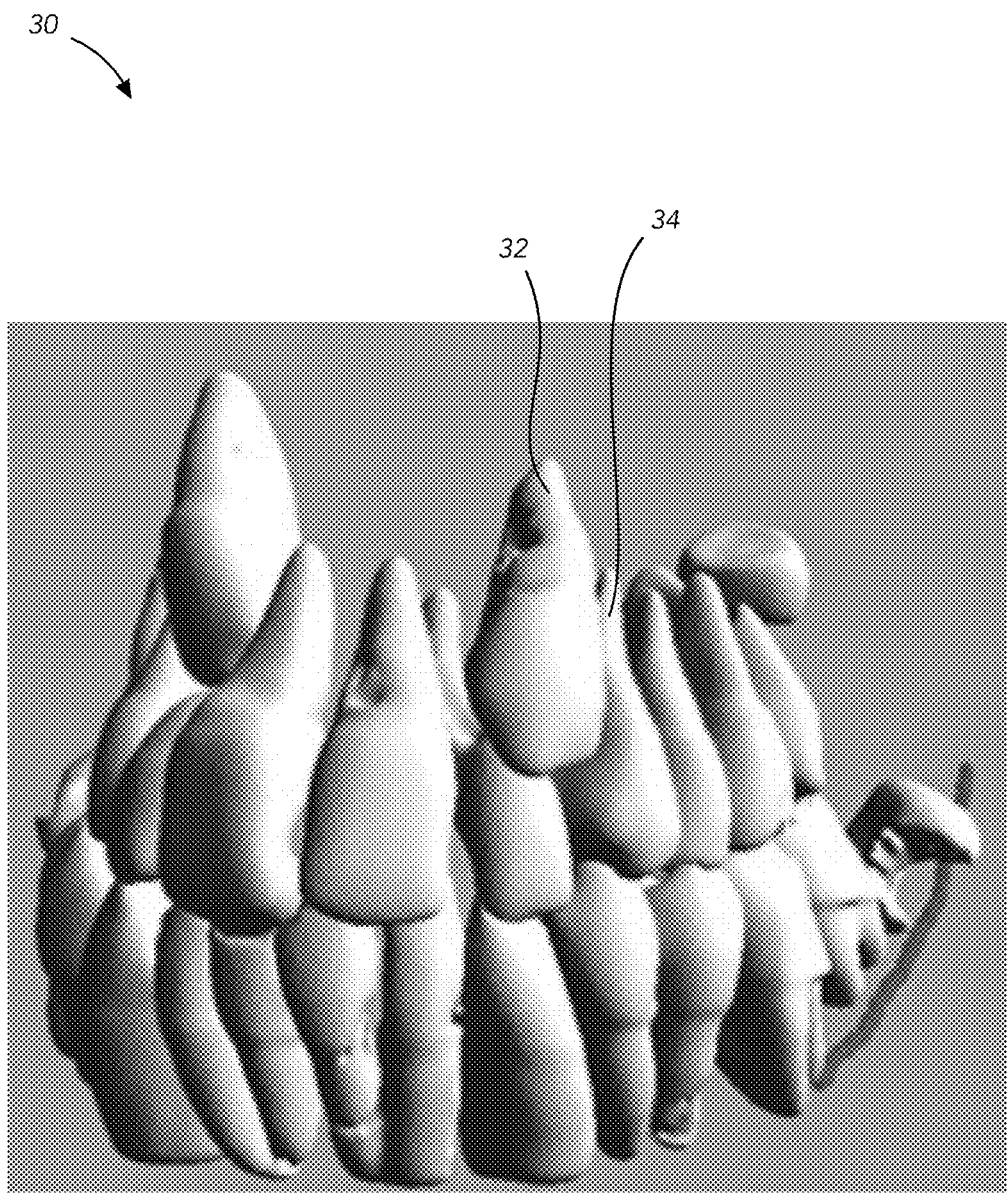
FIGS. 3A, 3B and 3C illustrate segmentation and graphical manipulation of teeth of a subject from an exemplary CBCT data set.
Figure 3B:
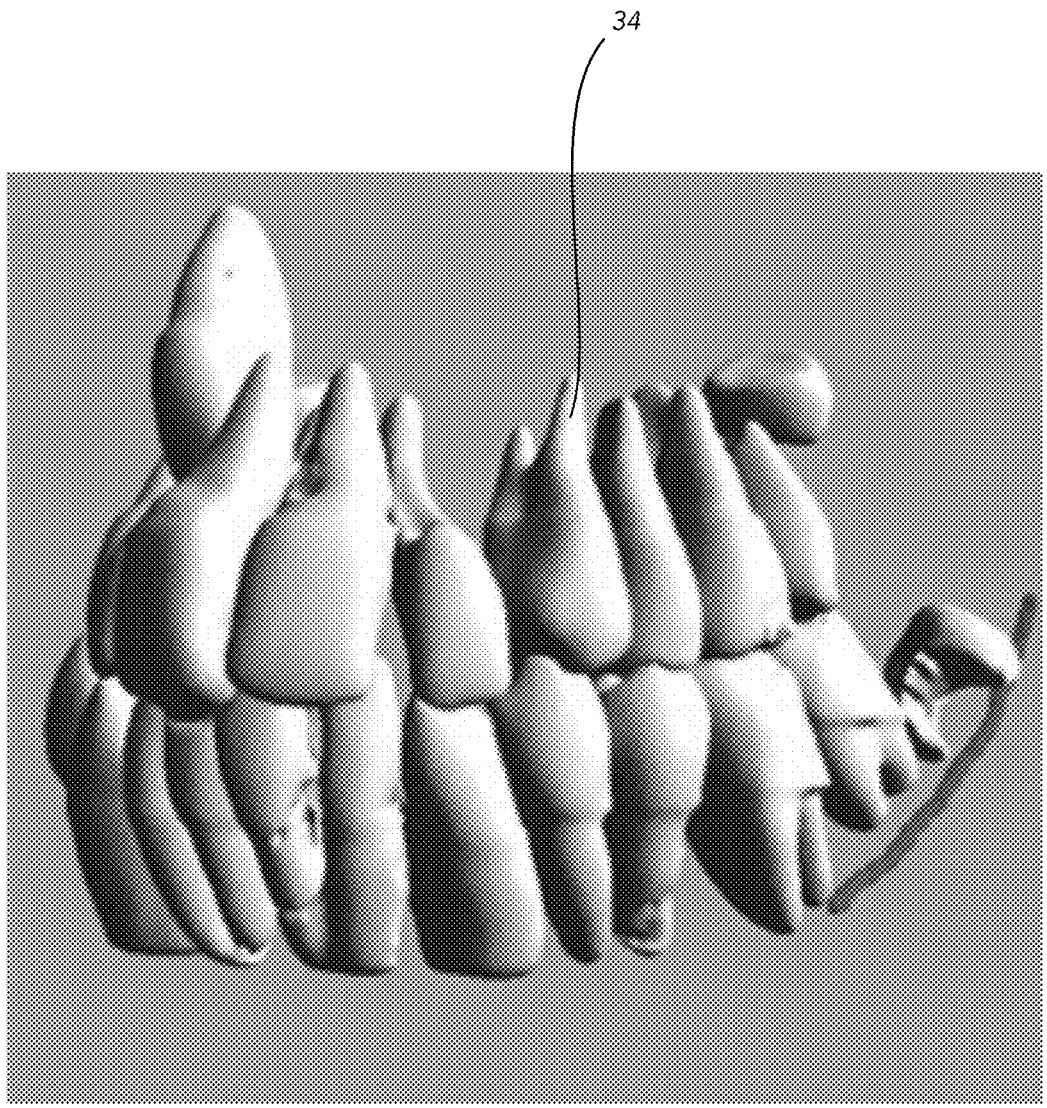

FIG. 3A is a further illustration of segmentation of a patient's teeth 30 from a CBCT data set. Note that the output on which FIG. 3A is based is a 3D data file, of which FIG. 3A is a 2D representation shown only for illustration. The segmentation 30 shown in FIG. 3A includes a tooth 32 which has been separately segmented. In the illustration of FIG. 3B, tooth 32 has been completely removed from the image. Segmentation 30 also includes a separately segmented tooth 34, which is visible in both FIGS. 3A and 3B, and is displayed in isolation in FIG. 3C.

Figure 3C:
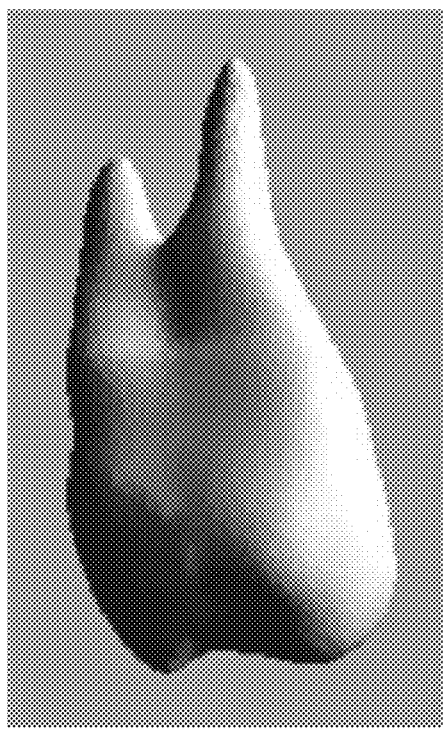

In one embodiment, the format of the segmented data files represented by FIGS. 3A, 3B and 3C may be compatible with a computer-aided design (CAD) software program, such that a user may view one or more segmented images on a screen and manipulate the location and orientation of the segmented images. FIG. 3C illustrates an example in which a 3D image of a particular tooth 24 is viewed in isolation. FIG. 3A illustrates an example in which a 3D image of a tooth 32 may be manipulated with respect to images of neighboring teeth for the purpose of treatment planning or diagnosis.

The data files representing the teeth can be segmented in a number of ways, for example, (a) as one data set representing the plurality of the subject's teeth all together, and/or (b) separately as individual representations of the subject's teeth where each tooth is represented separately from the others. The system and method can do either or do both of the foregoing segmentations or representations as suits a given need.

In the example (a) above, the spatial volume, pixels, or data points representing the subject's teeth volume can be presented, saved to a data file or data structure, or other representation of the overall extent of the subject's teeth. That is, the segmented image or data file can indicate collectively as one file or image everywhere any teeth are determined to exist in the 3D image space of the image or corresponding data set. No differentiation among the individual teeth is made in the representation. This representation may be saved to a single data set in a computer-readable medium or data file.

In the example (b) above, the present system and method can identify, segment or differentiate individual teeth from the plurality of a subject's teeth. This may be performed in a variety of ways. In one instance, the collective teeth are first segmented as described in method (a) above, then, the individual teeth are separated into individual data sets or image objects. Alternatively, the method and system can segment each individual tooth according to method (b) above first, and the collective tooth volume (a) is obtained by merging all of the individual teeth into one total tooth volume representation. The segmented data or image files described herein can take on a variety of technical forms, including STL RAW or STL formats, but this is not a requirement nor is it limiting of the present examples.

The foregoing and other examples show how the present invention causes the creation of stand-alone data objects representing corresponding anatomical object, which enables manipulation and deeper study of the objects. In some aspects, the invention is configured and arranged to create useful digital representations (data objects) of particular anatomical objects in a patient's body such as in the dental or similar areas. Those skilled in the art may see how this system and method could be extended to identifying and segmenting and generating output data objects of other anatomical features, organs, or bodily objects as well. This generalization is comprehended by the present disclosure and is meant to be covered wherever appropriate by the present disclosure and claims.

Figure 4:
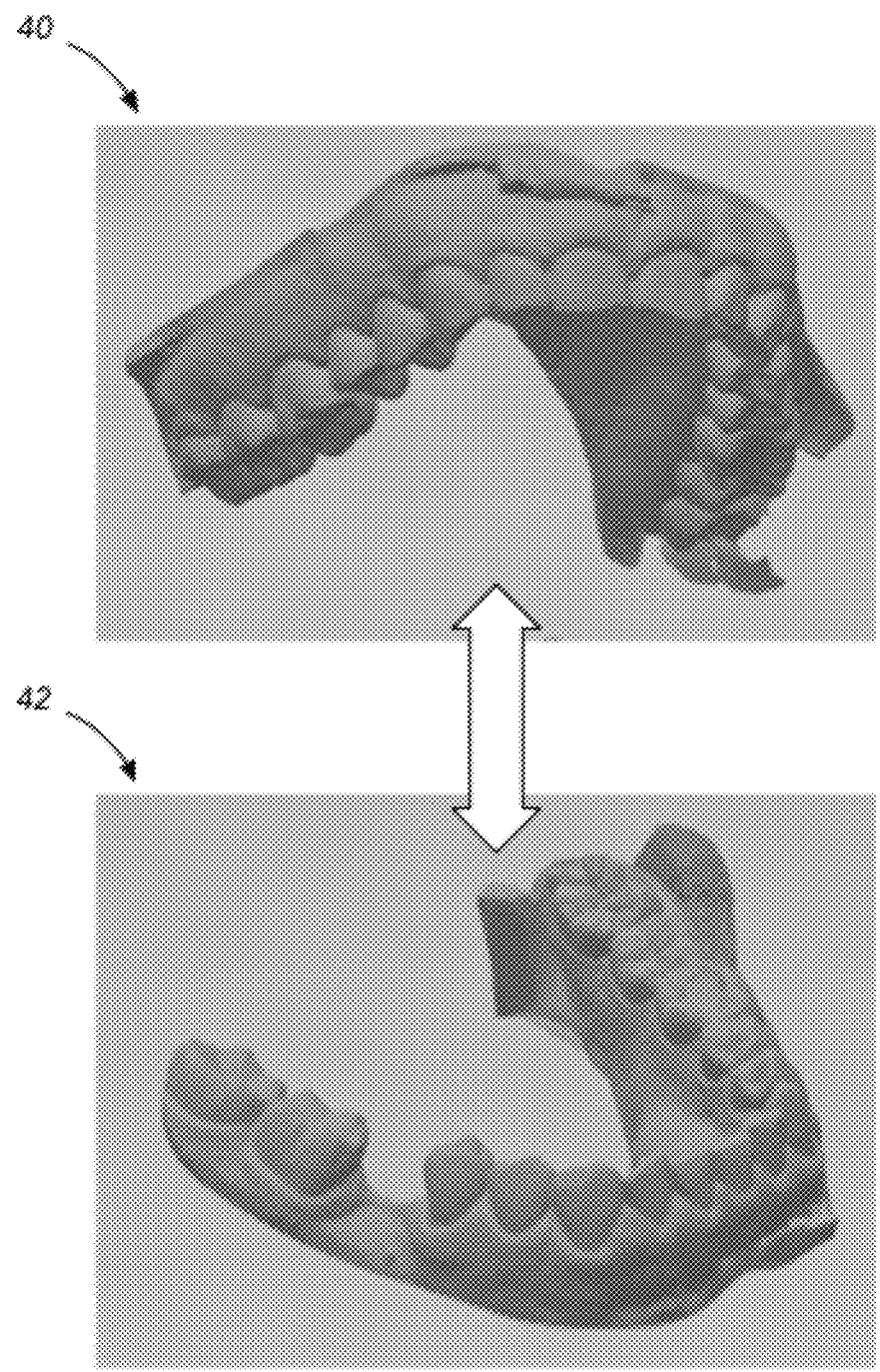
FIG. 4 illustrates an exemplary intra-oral scan model.

FIG. 4 illustrates another source of information used in embodiments of the present system and method. The internal volume of a subject's mouth can be represented by IOS data obtained from optical scans, imaging or mechanical molds taken from the subject's mouth to provide the contours of the intra-oral volume of the subject. In one non-limiting example, a deformable material can be used within the subject's oral cavity to form a mold matching the surface of the cavity, then the mold can be set and scanned, e.g., optically, to obtain a 3D data representation of the subject's unique intra-oral cavity or structures therein. The figure shows IOS data can provide high-resolution information regarding the cavities and solid surfaces (teeth and tissues) within the mouth. The intra-oral scan by any of these means can be digitized and used as an input to the present system and method, in combination with the afore-mentioned CBCT segmentation data. The subject's maxilla 40 and mandible 42 bones can be segmented using source CBCT data and visualized separately from the other structures such as the teeth in some embodiments. Still, as described, the system and method are configured and arranged to take as inputs the information derived from the IOS data, then apply the present machine learning technique to identify and segment one or more anatomical features of interest based on the machine learning identification thereof. Then, a corresponding data object is output by the system and method as described to comprise a special data object of that physical anatomical feature, which data object can then in turn be further analyzed and handled or viewed or processed.

Figure 5:
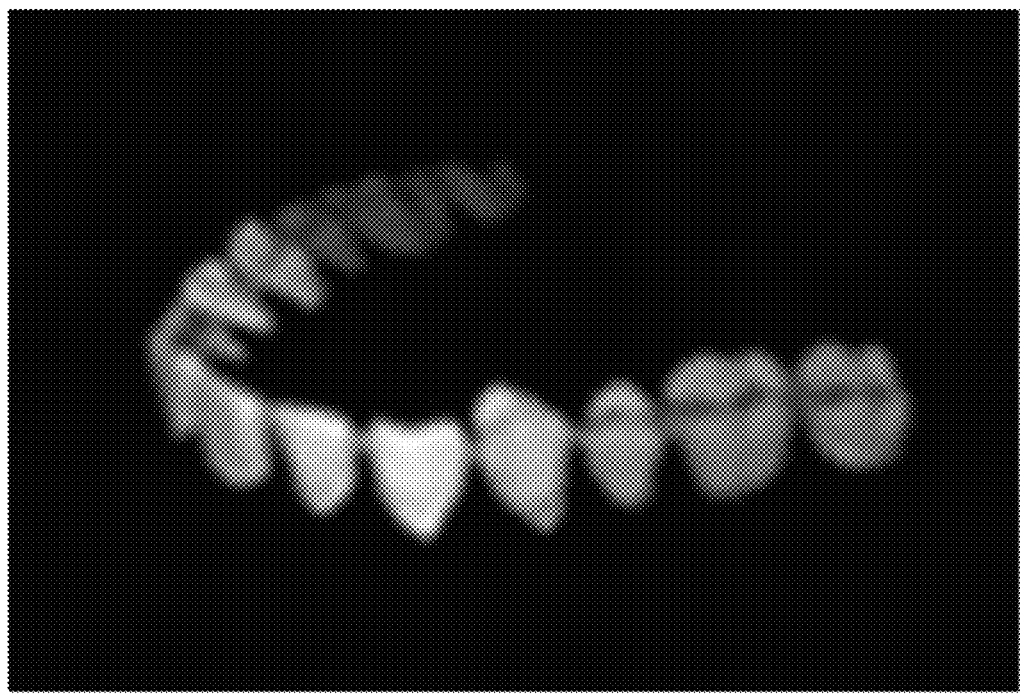
FIG. 5 illustrates an exemplary tooth crown model according to the prior art.

FIG. 5 illustrates an exemplary visualization 50 (from the prior art) showing the crowns of a subject's teeth, wherein a crown refers to those portions of the teeth, usually covered by enamel, which are imaged in the IOS data. In various embodiments, this system and method can also be used to extract, segment, or visualize the crown portions of one or more teeth. The crown portion(s) of the teeth may be segmented using either the CBCT data and/or the IOS data. In some embodiments, the present system and method can combine the crown portions of the teeth with the other portions of the teeth such as the roots of the teeth, which are normally not visualized by an intra-oral cavity mold. The result can be a combined image of great clinical utility to practitioners in the field. Such information can be utilized by the present system and method in the present new way to take the capabilities of patients and providers further insofar as the prior art imaging or imprinting inputs can be exploited using the invention's machine learning techniques to generate the illustrated data objects shown.

In an aspect, the present method and system are configured, programmed, adapted or otherwise arranged to permit visualization of a subject's teeth including the crowns obtained from intra-oral scans and the roots obtained from CBCT segmentation, which are then presented or stored together in a combined form representing the entire tooth or teeth in question. A full appreciation of the tooth or teeth, with or without the jawbone structures, and with or without other soft tissue structures are thus available in a way that was previously not possible in the prior art using the above-mentioned traditional methods.

Figure 6:
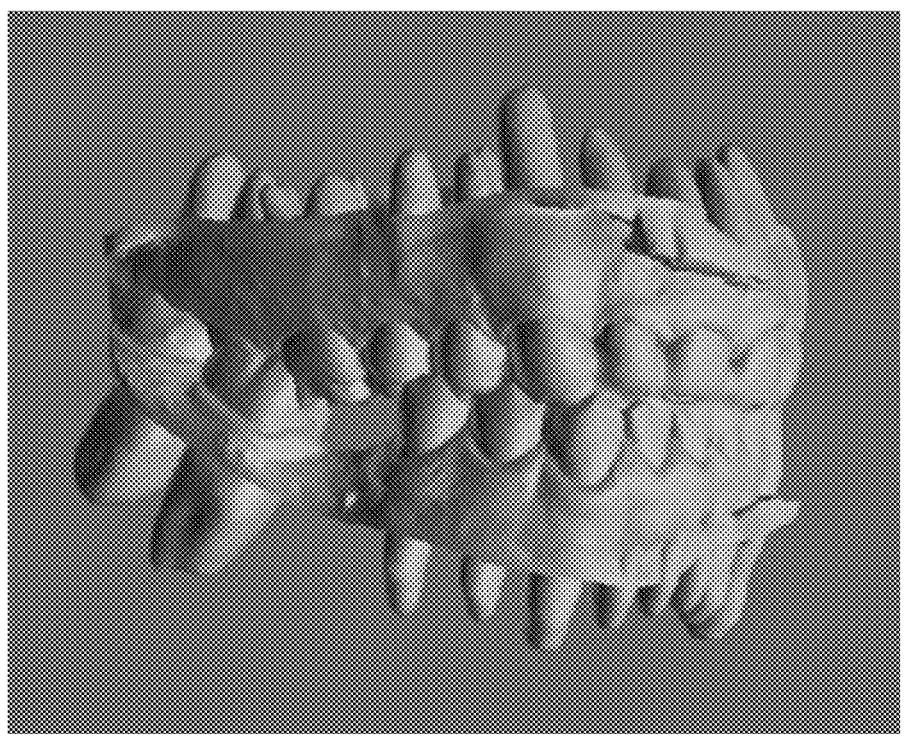
FIG. 6 illustrates a combined output of CBCT and intra-oral models following segmentation and processing according to an embodiment.

FIG. 6 illustrates an exemplary image or data file representation 60 of a subject's oral structures according to an embodiment of the present system and method. In the figure, segmented teeth from IOS data are shown registered over the same teeth segmented from CBCT data. The representation and/or data set are amenable to examination and analysis to determine a condition of a patient. The representation and/or data set are adapted for separately studying or displaying different types of structures such as the: tooth crowns, tooth roots, complete tooth or teeth, jawbones, and other proximal tissues.

Figure 7:
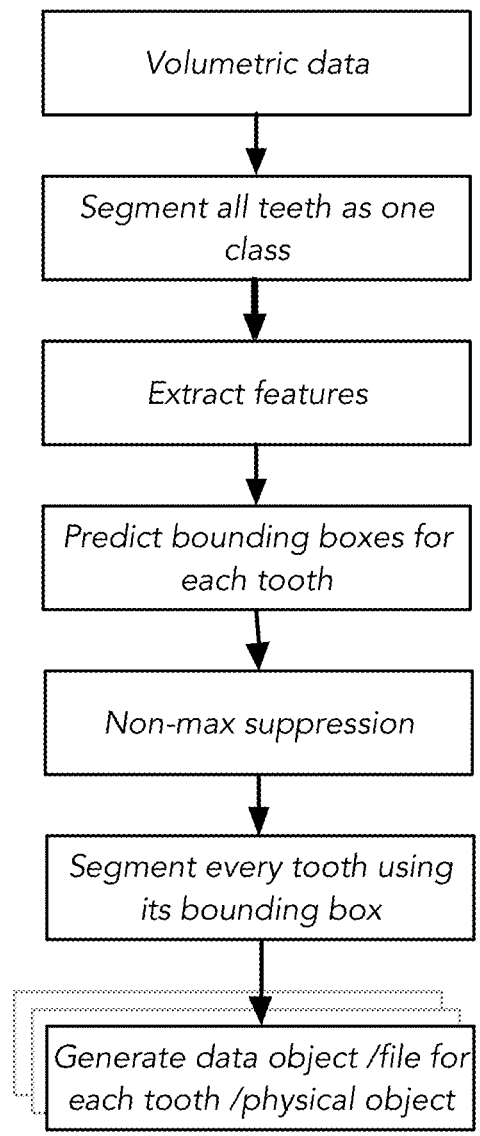
FIG. 7 illustrates an instance-aware segmentation method.

FIG. 7 illustrates an exemplary instance-aware segmentation method 70, wherein instance-aware segmentation treats multiple objects of the same class as distinct individual objects or instances. Method 70 includes steps of a computer-programmable or machine-readable instruction set implemented in a computing apparatus. First, volumetric (3D) data is obtained using one or more of the methods described above. Second, all of a subject's teeth are segmented as one class of data or objects in a combined fashion as mentioned earlier. Third, features of interest are extracted from the segmented image or data set. Fourth, bounding boxes, for example 3D bounding boxes, are predicted for each separate tooth of interest, providing the respective tooth's estimated location in the volume. Fifth, a non-max suppression process is applied to the segmented objects. The non-max suppression process transforms a smooth response map that triggers many imprecise object window hypotheses into a single bounding box for each detected object, effectively collapsing multiple bounding boxes of the same tooth into a single one. Sixth, each tooth of interest is separately segmented using its corresponding bounding box. Seventh, a STL or other data file is generated for each tooth of interest. It is to be appreciated that this sequence of steps is exemplary, and that those skilled in the art will appreciate that variations on this sequence are possible, including by adding or removing some of the steps as best suits a given implementation.

Figure 8:
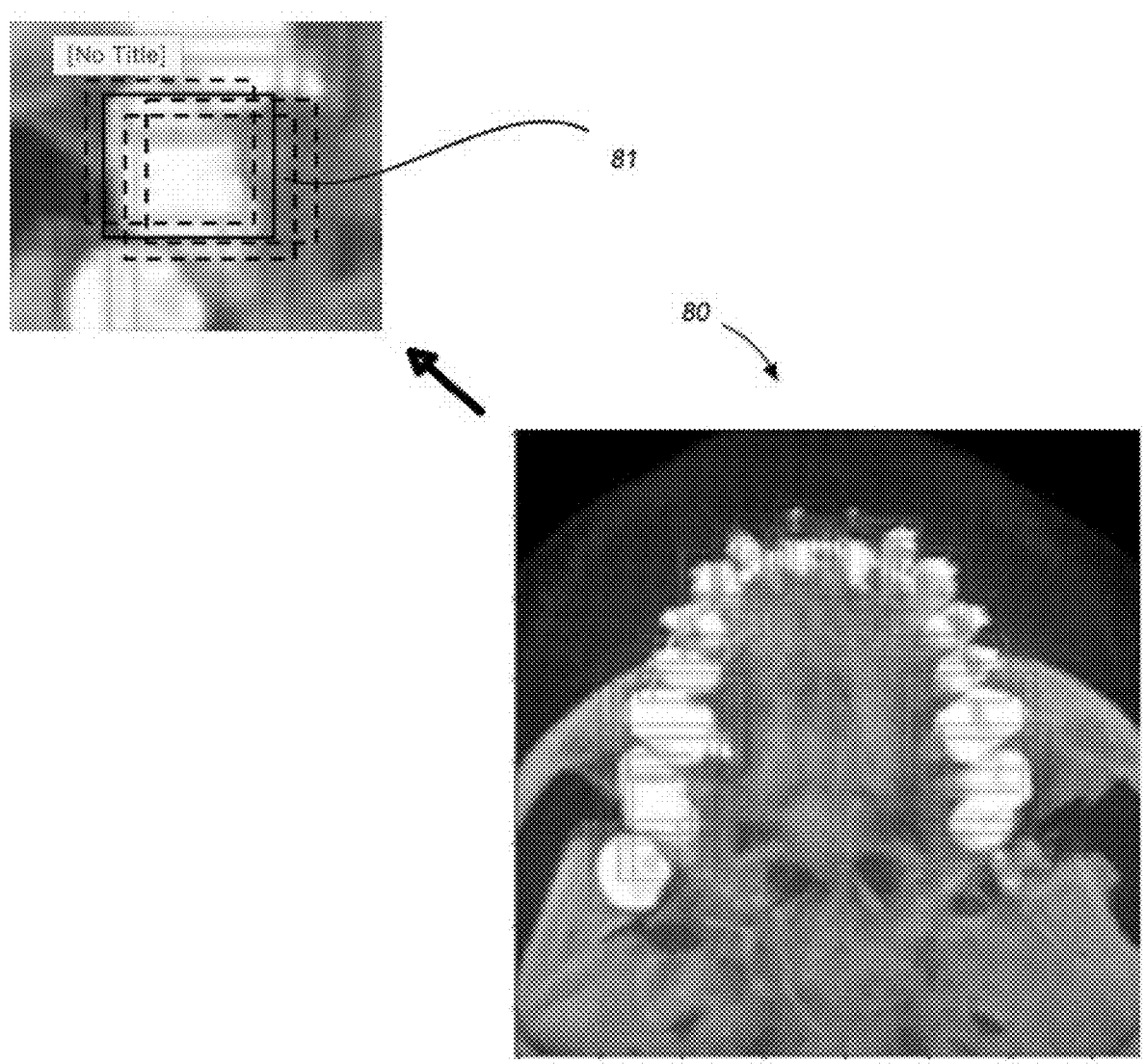
FIG. 8 illustrates collapsing multiple bounding boxes for a tooth into one box.

FIG. 8 illustrates results 80 of a non-max suppression process for collapsing multiple bounding boxes per tooth into a single bounding box 81 per tooth. Those skilled in the art will understand that the present discussions and illustrations apply to three-dimensional images and data.

The present system and method employ, in an aspect, machine learning, artificial intelligence and similar technologies to enhance the efficiency, accuracy and usefulness of the results. For example, the method and system employ in some embodiments a convolutional neural network (CNN), a fuller description of which can be found in the literature on this subject, for example as found at the time of this disclosure at http URL cs231n.github.io/convolutional-networks/.

For a CNN, the convolution is performed on the input data by means of a filter or kernel. The present system and method can employ 4D kernels of a volume equal to the shape (depth×height×width×num_channels) where num_channels is the number of channels in the output of a previous layer (last tensor dimension), and the depth-width-height are obtained from the convolution specification used in the method. The convolution method can sample all input channels, and can be computed for each spatial location or voxel in an image volume, or only at voxels where kernel samples are valid. In this method, activation is a function applied element-wise to an input tensor.

Some steps in the present technique employ ReLU and/or max pooling. ReLU activation is a function that is equal to zero if its argument is less than zero, or to the argument's value otherwise. Pooling layers perform spatial reduction. Specifically, a max pooling operation of size (m×n) replaces an (m×n) area of input channel with the maximum value in the area, (see, for example, descriptions of pooling generally, e.g., http URL cs231n.github.io/convolutional-networks/#pool incorporated herein by reference). The operation is applied channel-wise. The pooling operations in the above architecture have strides equal to pooling size. Preferably, the stride is the shift between pools and thus they do not intersect and there are no gaps between them. The pooling may permit windowing or cropping of the computational field in an image so as to merge, correlate, combine, shrink, reshape or otherwise reconfigure the computational dimensions or areas under consideration in an image.

In a neural network, a dense layer is a fully connected neural network layer in which each input node is connected to each output node. Dense layers compute a matrix multiplication of an input vector by a coefficient matrix. If a layer before a dense layer produces a tensor, that tensor is reshaped to a vector before multiplication. This operation accumulates data statistics and normalizes unit activations to have a Gaussian distribution, thereby improving network convergence. A dropout layer is similar to a dense layer, except that in a dropout layer the activations are set to zero for some random nodes. This is a way to prevent network overfitting.

Batch normalization is a method of initializing neural networks by explicitly forcing the activations throughout the network to take on a unit gaussian distribution at the beginning of the training. This operation improves network convergence.

To assess network performance, one or more objective loss functions may be implemented. One example is the so-called softmax cross-entropy objective loss function. Softmax is implemented in a neural network layer just before the output layer and assigns decimal probabilities to each class in a multi-class problem. The softmax layer must have the same number of nodes as the output layer. Cross-entropy loss measures the performance of a classification model whose output is a probability value between 0 and 1. Another example of an objective loss function is a mean squared error objective function for vectors to measure mean squared error between two vectors. The loss function is used to train a neural network in a machine learning processor and method, wherein weighting factors are changed to minimize said loss function. The invention is not limited to the recited loss functions, and those skilled in the art would employ these or other loss functions as suits their given application.

Figure 9:
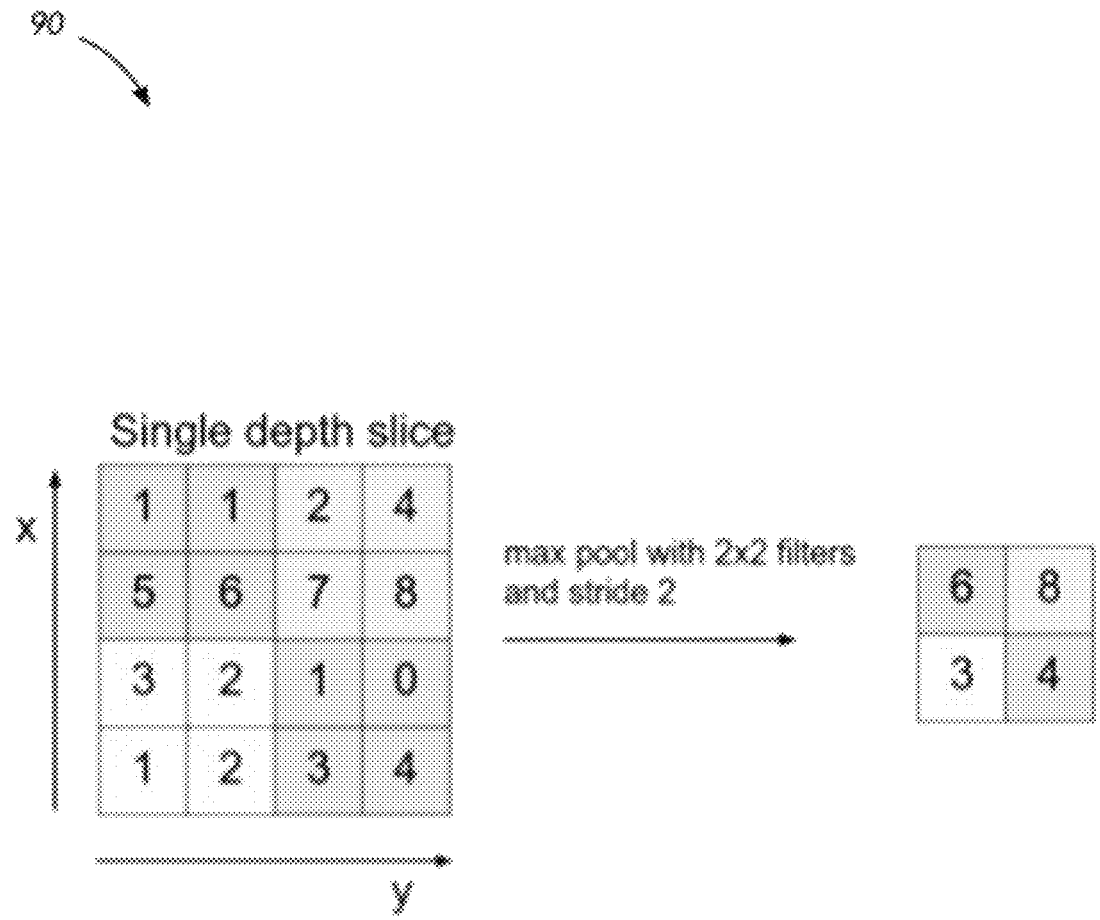
FIG. 9 illustrates an exemplary max pooling procedure according to the prior art usable in some examples.

FIG. 9 illustrates an exemplary 2×2 max pooling operation 90 that can be employed in aspects of the present method and system according to the present disclosure. While the max pooling operation can be adapted from the prior art, its adaptation for the present problem can be unique and was technically solved by the present inventors. The illustrated 2D operation is extendable to 3D but is illustrated in two dimensions for simplicity.

The present invention can be implemented in and with special computing hardware, software and/or firmware. The computer system of the present invention can comprise a stand-alone computing system in a client, server, or combined client-server architecture, including cloud-based data stores or processing hardware and software as best suits a given implementation. The following describes models and architectural aspects of exemplary embodiments of this invention, which are not to be taken as comprehensive or exhaustive of the several ways the invention can be used and applied. Those skilled in the art will, upon review of this disclosure, understand other equivalent embodiments comprehended by this disclosure as well.

Generally, the present system and method may be applied using the following neural network models:
1. Teeth area detection.
2. Teeth segmentation.
3. Teeth centers segmentation.
4. Jaws (bones) segmentation.

Teeth Area Detection

For teeth detection, the system and method accepts volumetric data such as 3D tensor data. In one non-limiting example, the data can be a 50-voxel cube of information, but this is extendable as needed. The input volume can be scaled to this size and normalized to a range of [0, 1] in an aspect. Trainable layers use weights obtained during the training. In this context, training comprises a process, method, steps or executable machine instructions that can be programmed into and/or stored in a storage unit, and carried out for example in a processing unit such as a training module. The training steps determine a model with coefficients that result in accurate prediction. The training process is automated, and in one embodiment uses a variation of the gradient descent method, which is a first-order iterative optimization algorithm for finding the minimum of a function. Search starts from a random initialization and goes in the direction opposite to loss function derivatives.

In one example, the model predicts several (e.g., six) floating point numbers, which are 3D coordinates of two opposite vertices of the detected bounding box. Coordinates are normalized in an example to a range [0, 1].

The following steps or an equivalent process may be carried out in an exemplary process by the present system and method:
1. 3D convolution 3×3×3, 64 filters, valid padding (output shape 48×48×48×64)
2. ReLU activation (output shape is the same)
3. Max-pooling 2×2×2 (output shape 24×24×24×64)
4. 3D convolution 3×3×3, 96 filters, valid padding (output shape 22×22×22×96)
5. ReLU activation (output shape is the same)
6. Max-pooling 2×2×2 (output shape 11×11×11×64)
7. 3D convolution 3×3×3, 128 filters, valid padding (output shape 9×9×9×128)
8. ReLU activation (output shape is the same)
9. Max-pooling 2×2×2 (output shape 4×4×4×64)
10. 3D convolution 3×3×3, 256 filters, valid padding (output shape 2×2×2×256)
11. ReLU activation (output shape is the same)
12. Dense (fully connected) layer 2048×384 (output shape 384—vector with 384 elements, 2048≡2×2×2×256)
13. ReLU activation (output shape is the same)
14. Dense (fully connected) layer 384×192 (output shape 192—vector with 192 elements)
15. ReLU activation (output shape is the same)
16. Dense (fully connected) layer 192×64 (output shape 64—vector with 64 elements)
17. ReLU activation (output shape is the same)
18. Dense (fully connected) layer 64×6 (output shape 6—vector with 6 elements). Output of this layer is a network prediction.

The foregoing is, again, only provided by way of illustration, and is not limiting of the scope of the present disclosure or invention.

Teeth Segmentation

As stated, a tooth area segmentation phase is used, which can accept 3D volumetric data input. A voxel size of 0.5 mm can be used, but this is only one example and not limiting.

An exemplary teeth segmentation algorithm consists of the following high-level steps or an equivalent process:
1. Not instance-aware teeth segmentation.
   Returns a soft segmentation mask containing probabilities of each volume in the voxel being a tooth voxel.
2. Soft segmentation mask to mesh conversion.
   The step is performed if the complete STL model containing all teeth together (not split into separate instances) is required.
   Returns STL-like structure with teeth mesh in local volume coordinates.
3. Mesh transformation.
   The mesh returned at the previous step is transformed to global case coordinates. This takes into account CBCT resolution and patient position information. It is only necessary to make an STL model aligned with the original CBCT case. The required transformation also may depend on the target software (the software that will be used to open CBCT and the model) as different software vendors tend to treat CBCT meta-information (like position) differently.
4. Instance-aware segmentation.
   Splits the soft teeth segmentation mask into separate teeth instances. Returns a set of soft segmentation masks, one per tooth. Each tooth is also accompanied with meta-information about its location in the original case, the main tooth axis orientation, the rotated bounding box (according to the main tooth axis) and the tooth number.
5. Per-instance soft tooth segmentation mask to mesh conversion.
   Returns separate STL-like meshes for every tooth.
6. Per-instance tooth mesh transformation.
   Transforms meshes of every tooth to global CBCT coordinates.

Not instance-aware teeth segmentation may consist of the following exemplary steps:
1. Simple crop estimation algorithm.
   The algorithm analyzes voxel intensities and finds areas that do not contain data by comparing values with some threshold. Next it crops configurable distances from case bottom, top and left/right (relative to the center).
   This step is required to handle cases with large field of view that were very rare in the training set.

2. Teeth area detection algorithm.
   The teeth area detection algorithm is implemented with a relatively simple artificial neural network architecture predicting coordinates of the bounding box containing teeth.
   The goal of this step is to reduce processing time of the following teeth segmentation step as it depends on the size of the volume it segments.
3. Teeth segmentation algorithm.
   The teeth segmentation algorithm is implemented with a 3D segmentation neural network similar to the U-Net algorithm. It accepts input volume of fixed spatial resolution (0.2 mm) and returns probabilities of each voxel being a tooth voxel.
   This network requires significant graphics processing unit (GPU) resources and is also limited by the amount of the available GPU memory. The algorithm therefore implements a tiling strategy with configurable overlapping. Tile sizes are configurable but can also be chosen automatically depending on the available GPU memory.
4. Active contours refinement algorithm.
   Uses a Geodesic Active Contours algorithm to refine teeth segmentation using the original CBCT data. The algorithm tries to find edges in the data that are near to the found segmentation and adjusts segmentation towards these edges.

Instance-aware teeth segmentation may consist of the following exemplary steps:
1. Simple crop estimation algorithm.
   The same algorithm as for "not instance-aware" segmentation.
2. Teeth area detection algorithm.
   The same algorithm as for "not instance-aware" segmentation.
3. Teeth centers segmentation algorithm.
   A neural network trained to segment teeth internals (centers). The goal is to get separate groups of voxels that are used in the next step as a seed for the watershed algorithm.
4. Teeth splitting.
   Uses not instance-aware teeth segmentation and teeth centers obtained at the previous steps to split the complete teeth mask into separate instances. The teeth splitting algorithm is based on the watershed algorithm, which is a classical algorithm used for segmentation.
5. Symmetry estimation.
   Finds the vertical symmetry plane of the CBCT case. The search is performed on a 2D slice of the original data. The symmetry plane is used to separate teeth as belonging to the left or right part of the jaws in the next step.
6. Teeth numbers assignment.
   Numbers assignment uses the symmetry plane to find teeth belonging to the left and right parts of the jaws and uses k-means clustering to split teeth into mandible and maxilla teeth. After these splits are found, teeth are assigned consecutive numbers within a single quarter starting from the jaw's center.
7. Per-tooth main axis estimation.
   This step uses principal component analysis (PCA) to find the main axis of the tooth. The axis is used to build a tight (rotated) bounding box and also to make a roots filtering step. Taking the main axis into account improves performance for inclined teeth.
8. Per-tooth roots filter.
   Images of teeth roots often have low intensity, and this step takes the low intensity into account by applying different processing parameters to the roots/crown area.
9. Per-tooth active contours refinement.
   Uses a Geodesic Active Contours algorithm to refine segmentation of each tooth using the original CBCT data. The algorithm tries to find edges in the data that are near to the found segmentation and adjusts segmentation toward these edges.

For example, a teeth segmentation may be applied using these steps or an equivalent process, noting that the "?" character refers to integer numbers that would be selected based upon a given application:
1. 3D convolution 3×3×3, 32 filters, same padding (output shape ?×?×?×32)
2. Batch normalization (output shape is the same)
3. ReLU activation (output shape is the same)
4. 3D convolution 3×3×3, 64 filters, same padding (output shape ?×?×?×64), stride=2
5. Batch normalization (output shape is the same)
6. ReLU activation (output shape is the same)
7. 3D convolution 3×3×3, 64 filters, same padding (output shape ?×?×?×64)
8. Batch normalization (output shape is the same)
9. ReLU activation (output shape is the same)
10. 3D convolution 3×3×3, 128 filters, same padding (output shape ?×?×?×128), stride=2
11. Batch normalization (output shape is the same)
12. ReLU activation (output shape is the same)
13. 3D convolution 3×3×3, 128 filters, same padding (output shape ?×?×?×128)
14. Batch normalization (output shape is the same)
15. ReLU activation (output shape is the same)
16. 3D convolution 3×3×3, 256 filters, same padding (output shape ?×?×?×256), stride=2
17. Batch normalization (output shape is the same)
18. ReLU activation (output shape is the same)
19. 3D convolution 3×3×3, 256 filters, same padding (output shape ?×?×?×256)
20. Batch normalization (output shape is the same)
21. ReLU activation (output shape is the same)
22. 3D convolution 3×3×3, 512 filters, same padding (output shape ?×?×?×512)
23. Batch normalization (output shape is the same)
24. ReLU activation (output shape is the same)
25. 3D Deconvolution 2×2×2, 512 filters (output shape ?×?×?×512)
26. Channel concatenation of layers 25 and 15 output (output shape ?×?×?×640, 640=512+128)
27. 3D convolution 3×3×3, 256 filters (output shape ?×?×?×256)
28. Batch normalization (output shape is the same)
29. ReLU activation (output shape is the same)
30. 3D convolution 3×3×3, 256 filters (output shape ?×?×?×256)
31. Batch normalization (output shape is the same)
32. ReLU activation (output shape is the same)
33. 3D Deconvolution 2×2×2, 256 filters (output shape ?×?×?×256)
34. Channel concatenation of layers 33 and 9 output (output shape ?×?×?×320, 320=256+64)
35. 3D convolution 3×3×3, 128 filters (output shape ?×?×?×128)
36. Batch normalization (output shape is the same)
37. ReLU activation (output shape is the same)

38. 3D convolution 3×3×3, 128 filters (output shape ?×?×?×128)
39. Batch normalization (output shape is the same)
40. ReLU activation (output shape is the same)
41. 3D Deconvolution 2×2×2, 128 filters (output shape ?×?×?×128)
42. Channel concatenation of layers 41 and 3 output (output shape ?×?×?×160, 160≡128+32)
43. 3D convolution 3×3×3, 64 filters (output shape ?×?×?×64)
44. Batch normalization (output shape is the same)
45. ReLU activation (output shape is the same)
46. 3D convolution 3×3×3, 64 filters (output shape ?×?×?×64)
47. Batch normalization (output shape is the same)
48. ReLU activation (output shape is the same)
49. 3D convolution 1×1×1, 2 filters (output shape ?×?×?×2). Output of this layer is a network prediction.

When segmentation is complete, an output mask is applied, wherein, in an embodiment, the mask is scaled to the source volume size using linear interpolation and binarized. The mask is scaled to the source volume size using linear interpolation and binarized. Then the mask is converted to a 3D mesh. Each outer face of voxels is converted to two triangles in one example. To smooth the mesh, a Laplacian smoothing step or other equivalent smoothing operation may be used. The invention is not limited strictly to the provided examples, which are given for the sake of illustration. Rather, one skilled in the art may choose equivalent or alternate features to implement a desired embodiment of the invention based on specific needs.

Teeth Centers Segmentation

The teeth centers algorithm accepts volumetric data (3-dimensional tensor) of any size but expects specific resolution. Voxel size should be 0.5 mm. The input volume is scaled to have a specified voxel size and is normalized to range [0, 1.0] before next steps. All trainable layers use weights obtained during the training. The model outputs 2 floating point numbers for each input voxel. For an input shape D×H×W output shape will be D×H×W×2. These numbers are class scores of two exclusive classes: is a tooth center, is not a tooth center. The model is trained on the modified annotated data—the teeth annotations are eroded and contain only internal parts of teeth. In an aspect, this allow obtaining separable groups of voxels belonging to different teeth.

For example, a teeth centers segmentation may be applied using these steps or an equivalent process:

1. 3D convolution 3×3×3, 32 filters, same padding (output shape ?×?×?×32)
2. Batch normalization (output shape is the same)
3. ReLU activation (output shape is the same)
4. 3D convolution 3×3×3, 64 filters, same padding (output shape ?×?×?×64), stride=2
5. Batch normalization (output shape is the same)
6. ReLU activation (output shape is the same)
7. Max-pooling with 2×2×2 size (output shape ?×?×?×64)
8. 3D convolution 3×3×3, 64 filters, same padding (output shape ?×?×?×64)
9. Batch normalization (output shape is the same)
10. ReLU activation (output shape is the same)
11. 3D convolution 3×3×3, 128 filters, same padding (output shape ?×?×?×128), stride=2
12. Batch normalization (output shape is the same)
13. ReLU activation (output shape is the same)
14. Max-pooling with 2×2×2 size (output shape ?×?×?×128)
15. 3D convolution 3×3×3, 128 filters, same padding (output shape ?×?×?×128)
16. Batch normalization (output shape is the same)
17. ReLU activation (output shape is the same)
18. 3D convolution 3×3×3, 256 filters, same padding (output shape ?×?×?×256), stride=2
19. Batch normalization (output shape is the same)
20. ReLU activation (output shape is the same)
21. Max-pooling with 2×2×2 size (output shape ?×?×?×256)
22. 3D convolution 3×3×3, 256 filters, same padding (output shape ?×?×?×256)
23. Batch normalization (output shape is the same)
24. ReLU activation (output shape is the same)
25. 3D convolution 3×3×3, 512 filters, same padding (output shape ?×?×?×512)
26. Batch normalization (output shape is the same)
27. ReLU activation (output shape is the same)
28. 3D Deconvolution 2×2×2, 512 filters (output shape ?×?×?×512)
29. Channel concatenation of layers 28 and 20 output (output shape ?×?×?×768, 768≡512+256)
30. 3D convolution 3×3×3, 256 filters (output shape ?×?×?×256)
31. Batch normalization (output shape is the same)
32. ReLU activation (output shape is the same)
33. 3D convolution 3×3×3, 256 filters (output shape ?×?×?×256)
34. Batch normalization (output shape is the same)
35. ReLU activation (output shape is the same)
36. 3D Deconvolution 2×2×2, 256 filters (output shape ?×?×?×256)
37. Channel concatenation of layers 36 and 13 output (output shape ?×?×?×384, 384≡256+128)
38. 3D convolution 3×3×3, 128 filters (output shape ?×?×?×128)
39. Batch normalization (output shape is the same)
40. ReLU activation (output shape is the same)
41. 3D convolution 3×3×3, 128 filters (output shape ?×?×?×128)
42. Batch normalization (output shape is the same)
43. ReLU activation (output shape is the same)
44. 3D Deconvolution 2×2×2, 128 filters (output shape ?×?×?×128)
45. Channel concatenation of layers 44 and 6 output (output shape ?×?×?×192, 192≡128+64)
46. 3D convolution 3×3×3, 64 filters (output shape ?×?×?×64)
47. Batch normalization (output shape is the same)
48. ReLU activation (output shape is the same)
49. 3D convolution 3×3×3, 64 filters (output shape ?×?×?×64)
50. Batch normalization (output shape is the same)
51. ReLU activation (output shape is the same)
52. 3D convolution 1×1×1, 2 filters (output shape ?×?×?×2). Output of this layer is a network prediction.

Jaws Segmentation

The jaws segmentation algorithm accepts volumetric data (3-dimensional tensor) of any size but expects specific resolution. Voxel size should be 0.5 mm. Input volume is scaled to have a specified voxel size and is normalized to range [0, 1.0] before next steps. All trainable layers use weights obtained during the training. The model outputs 2 floating point numbers for each input voxel. For an input shape D×H×W, the output shape will be D×H×W×3. These numbers are class scores of three exclusive classes: mandible, maxilla, not a bone.

For example, a jaws segmentation may be applied using these steps or an equivalent process:

1. 3D convolution 3×3×3, 32 filters, same padding (output shape ?×?×?×32)
2. Batch normalization (output shape is the same)
3. ReLU activation (output shape is the same)
4. 3D convolution 3×3×3, 64 filters, same padding (output shape ?×?×?×64), stride=2
5. Batch normalization (output shape is the same)
6. ReLU activation (output shape is the same)
7. 3D convolution 3×3×3, 64 filters, same padding (output shape ?×?×?×64)
8. Batch normalization (output shape is the same)
9. ReLU activation (output shape is the same)
10. 3D convolution 3×3×3, 128 filters, same padding (output shape ?×?×?×128), stride=2
11. Batch normalization (output shape is the same)
12. ReLU activation (output shape is the same)
13. 3D convolution 3×3×3, 128 filters, same padding (output shape ?×?×?×128)
14. Batch normalization (output shape is the same)
15. ReLU activation (output shape is the same)
16. 3D convolution 3×3×3, 256 filters, same padding (output shape ?×?×?×256), stride=2
17. Batch normalization (output shape is the same)
18. ReLU activation (output shape is the same)
19. 3D convolution 3×3×3, 256 filters, same padding (output shape ?×?×?×256)
20. Batch normalization (output shape is the same)
21. ReLU activation (output shape is the same)
22. 3D convolution 3×3×3, 512 filters, same padding (output shape ?×?×?×512)
23. Batch normalization (output shape is the same)
24. ReLU activation (output shape is the same)
25. 3D Deconvolution 2×2×2, 512 filters (output shape ?×?×?×512)
26. Channel concatenation of layers 25 and 15 output (output shape ?×?×?×640, 640=512+128)
27. 3D convolution 3×3×3, 256 filters (output shape ?×?×?×256)
28. Batch normalization (output shape is the same)
29. ReLU activation (output shape is the same)
30. 3D convolution 3×3×3, 256 filters (output shape ?×?×?×256)
31. Batch normalization (output shape is the same)
32. ReLU activation (output shape is the same)
33. 3D Deconvolution 2×2×2, 256 filters (output shape ?×?×?×256)
34. Channel concatenation of layers 33 and 9 output (output shape ?×?×?×320, 320=256+64)
35. 3D convolution 3×3×3, 128 filters (output shape ?×?×?×128)
36. Batch normalization (output shape is the same)
37. ReLU activation (output shape is the same)
38. 3D convolution 3×3×3, 128 filters (output shape ?×?×?×128)
39. Batch normalization (output shape is the same)
40. ReLU activation (output shape is the same)
41. 3D Deconvolution 2×2×2, 128 filters (output shape ?×?×?×128)
42. Channel concatenation of layers 41 and 3 output (output shape ?×?×?×160, 160=128+32)
43. 3D convolution 3×3×3, 64 filters (output shape ?×?×?×64)
44. Batch normalization (output shape is the same)
45. ReLU activation (output shape is the same)
46. 3D convolution 3×3×3, 64 filters (output shape ?×?×?×64)
47. Batch normalization (output shape is the same)
48. ReLU activation (output shape is the same)
49. 3D convolution 1×1×1, 2 filters (output shape ?×?×?×2). Output of this layer is a network prediction.

Training Procedure

As to the machine learning or training aspects of the present invention, the following describes exemplary processes for enhancing the design and performance of the instant methods and systems. In an aspect, a training algorithm of a neural network model uses an existing set of training data from a corresponding domain. Each model is trained in a fully supervised setup, meaning that for each data sample in the training data set there is a known correct value that the model should predict. The correct values are further referred to as "ground truth" values.

In an aspect, each neural network model has an objective function (also referred as a "loss function") chosen at the model design step. This function establishes a quantitative measure of an error the model has on a particular sample.

The following illustrates an exemplary training method:
1. The weights in the trained neural network are initialized. An exemplary algorithm uses "Glorot uniform" initialization, in which each weight is initialized with a small Gaussian value with mean=0.0 and variance based on the fan-in and fan-out of the weight.
2. A forward pass is performed to compute the loss value for given input images. The forward pass consists of operations defined by the network architecture applied one after the other.
3. A backward pass is computed, which may use a backpropagation technique to compute loss gradients by model weights. Backpropagation is an algorithm for computing gradient, for example using a chain rule. The gradients may be used in a gradient descent step to optimize network weight factors. Other ways to compute gradients may be employed upon review of this disclosure by those skilled in the art without loss of generality and are equally comprehended hereby.
4. The model's weights are updated using one of the gradient descent methods. One example of such a method is an Adam optimizer (see https URL arxiv.org/abs/1412.6980)
5. The process repeats steps 1 to 4 over and over with different input samples until one of the following conditions is met:
    a. A target accuracy (difference between predicted and ground truth) is reached, or
    b. The difference between predicted and ground truth values is not decreasing or decreasing very slowly as the training proceeds.

Figure 10:
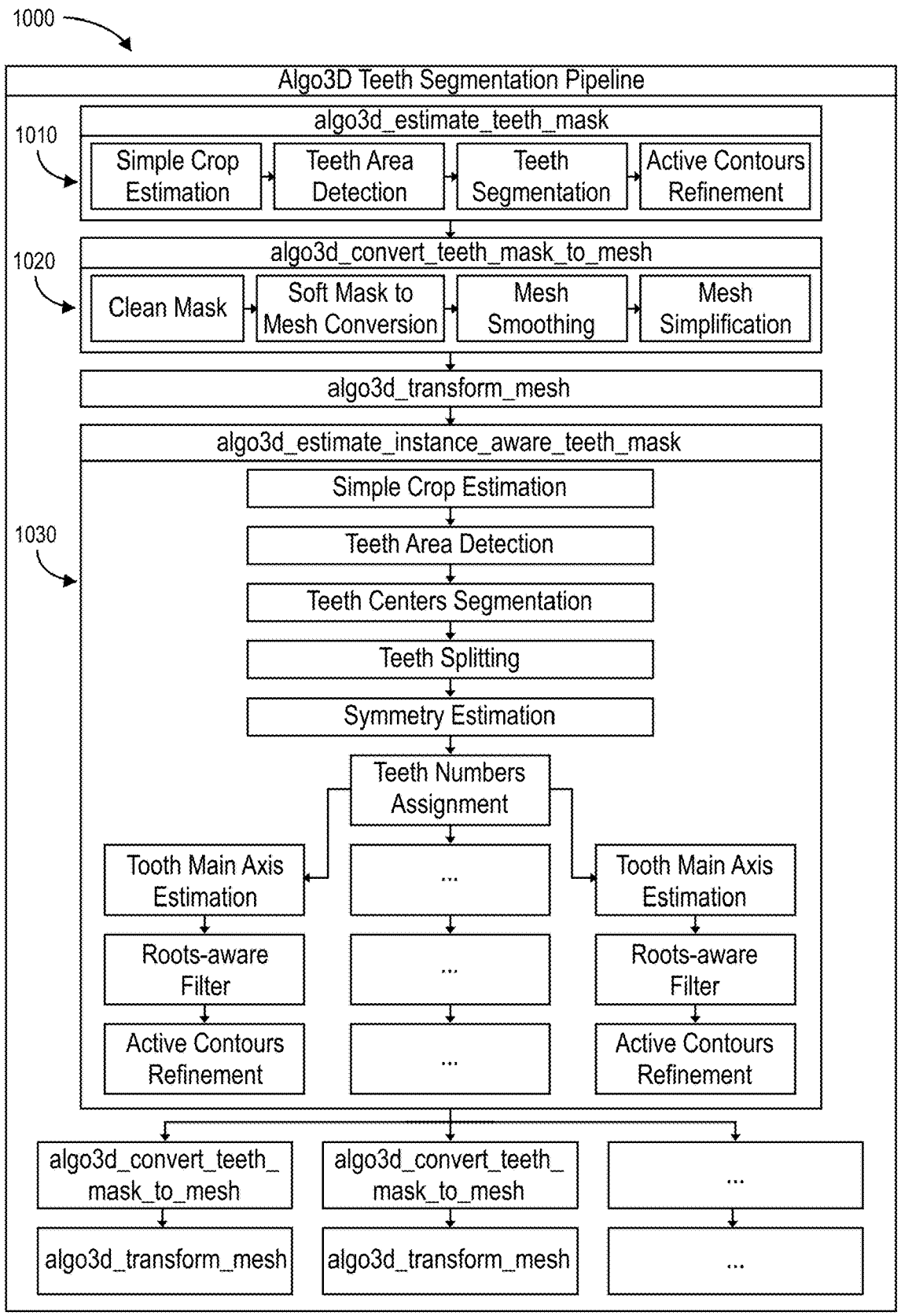
FIG. 10 illustrates an exemplary process for segmentation of teeth anatomy.

FIG. 10 illustrates exemplary steps and technical solutions according to this invention and by which the present system is configured and arranged. This exemplary method 1000 will achieve the 3D teeth segmentation result discussed earlier, and can be modified or applied to non-teeth segmentation applications by those skilled in the art. The steps may be grouped into routines 1010, 1020, 1030 and may be carried out individually or in batch mode as suits a given implementation without loss of generality.

Figure 11:
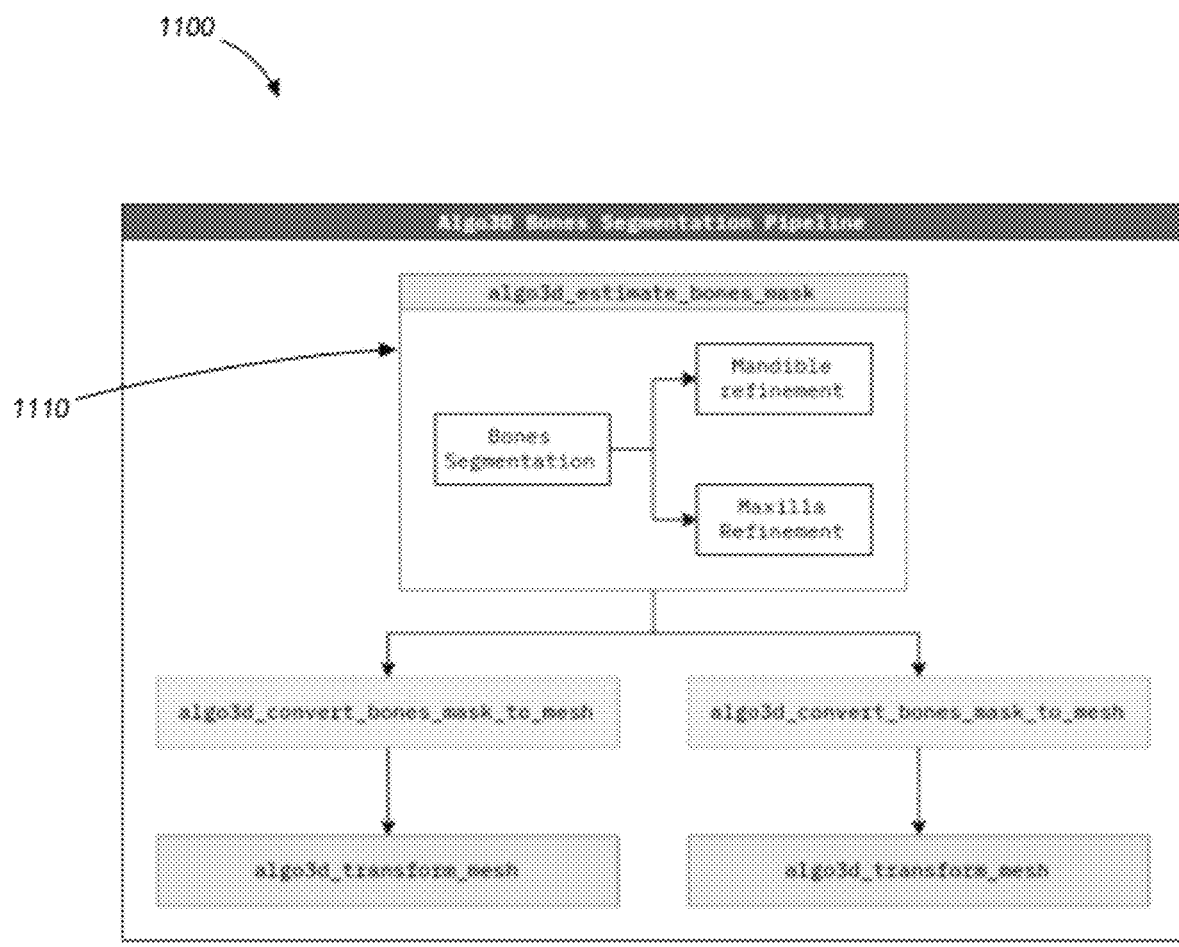
FIG. 11 illustrates an exemplary process for segmentation of bone anatomy.

FIG. 11 illustrates exemplary steps and technical solutions according to this invention and by which the present system is configured and arranged. This exemplary method 1100 will achieve the 3D bone segmentation result discussed earlier, and can be modified or applied to non-bone segmentation applications by those skilled in the art. The steps may be grouped into routines as shows at 1110 or may be carried out individually or in batch mode as suits a given implementation without loss of generality.

Therefore, it can be seen that the present disclosure is directed to systems and methods for processing and managing data, information and decisions in an information technology architecture. The architecture may comprise a server, client-server environment and/or cloud-based computing architecture. A processor or processors including electronic processing circuits may be designed and configured to execute special computer-readable instructions or programs. The circuitry and processor may be separate special circuits such as image processors that include a plurality of electronic logic units, transistors, and conducting lines and circuit elements to controllably and programmably actuate said logic in a semiconductor processor device according to the particular machine-readable instructions and input signals. The inputs can include one or more image data files such as the 3D dental image files described previously received from a medical imaging device such as an x-ray imager, CT scan imager and the like. The 3D images are processed in said medical image processing circuits to give a needed format or subset or superset of data that is used by a machine learning processor or engine in the system of this invention, the machine learning processor further coupled to a data store on which a plurality (usually many hundreds, thousands or more) learning database image data are available and from which the machine learning processor can act on and compare and determine one or more relevant aspects of the 3D image data. The system then uses a segmentation processing circuit to segment, isolate, indicate or otherwise discretely flag 3D data, pixels, voxels, or other data elements into a new 3D segmented data object representing an anatomical physical object of interest. A user interface (UI) may be used to take an input from a user through a UI input device and convert the user's input to an output to the segmentation processor and/or an output display device including a digital graphics processor to display the segmented 3D data object or a visual representation thereof to the user. Additionally, the UI may be used to enable the user to interact with the 3D segmented data object, including in some embodiments to select the data object, translate the data object, rotate the data object, make the data object be visible or invisible, and so on. As mentioned, this can in some examples enable the operator to simulate a dental procedure such as the removal of a segmented tooth or some other process useful for patients with impacted teeth or other clinical conditions under investigation.

The system and architecture may be designed and configured as best suits a particular application. For example, the elements of the system may be substantially co-located or in a same server computing device. Alternatively, some of the elements of the system may be remote from one another such as being coupled over a local or a wide area network or over the cloud (e.g., Internet).

Figure 12:
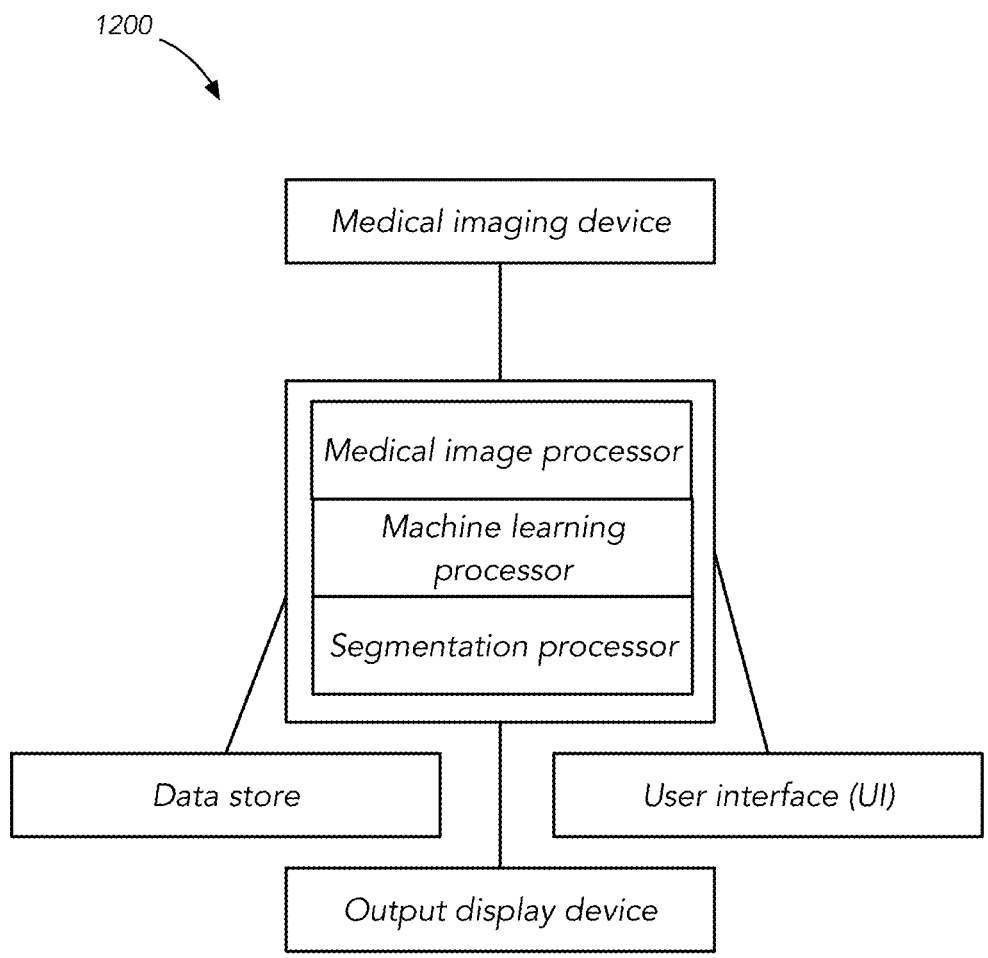
FIG. 12 illustrates an architecture for implementing the present invention.

As shown in FIG. 12, the system 1200 may include one or more processing circuits. These circuits can be separately implemented, e.g., using separate integrated circuit (IC) wafers or chips; or they may be implemented in shared circuitry on a same IC wafer or chip, and may include elements of a central processing unit (CPU) and/or graphical processing unit (GPU) and/or independent circuits altogether.

The present invention should not be considered limited to the particular embodiments described above, but rather should be understood to cover all aspects of the invention as fairly set out herein. Various modifications, equivalent processes, as well as numerous structures to which the present invention may be applicable, will be readily apparent to those skilled in the art to which the present invention is directed upon review of the present disclosure.

What is claimed is:

1. A method for automated processing of a three-dimensional (3D) dental image containing one or more bone structures and teeth within a teeth volume in a processor-based machine using machine learning steps, so as to provide results for treatment planning and follow-up, the method comprising:
    acquiring CT image data of said bone structures and teeth;
    acquiring intra-oral scan (IOS) data of said teeth;
    forming said three-dimensional dental image from both the acquired CT image data and the IOS data;
    receiving the three-dimensional dental image including an image of the one or more bone structures and the teeth within said teeth volume;
    performing a sequence of automated segmentation of anatomical features of the received dental image, including by tiling of configurably sized and overlapped tile regions, to produce segmented anatomical features, the segmentation based on machine learning from previously-analyzed dental images;
    creating a segmented data file corresponding to one or more of the segmented anatomical features;
    formatting the segmented data file so that the one or more segmented anatomical features are viewable by a user on a display device; and
    providing the segmented data file to the user,
    wherein the sequence of automated segmentation comprises:
        segmenting all of said one or more bone structures collectively as a first class, creating a collective segmented data file;
        segmenting all of said teeth collectively as a single class, creating a total segmented teeth volume data file that represents a total segmented teeth volume;
        predicting multiple predicted 3D bounding boxes for each tooth of a patient to provide a respective estimated location for each tooth within the total segmented teeth volume;
        collapsing, for each tooth, the multiple predicted 3D bounding boxes into a respective single 3D bounding box;
        segmenting each tooth separately using the respective single 3D bounding box; and
        generating a segmented tooth data file for each tooth.

2. The method of claim 1, wherein receiving the 3D dental image comprises receiving the 3D dental image of the one or more bone structures over a cloud-based communication network.

3. The method of claim 1, wherein the sequence of automated segmentation comprises using a convolutional neural network (CNN) process executed in the processor-based machine, and employing information from the previously-analyzed dental images, so as to segment the anatomical features in the 3D dental image.

4. The method of claim 1, wherein the 3D dental image comprises data from a dental cone beam computerized tomography (CBCT) device.

5. The method of claim 1, wherein the 3D dental image comprises data from one or more of a dental cone beam computerized tomography (CBCT) device, an intra-oral data acquisition device, and/or a scan of a denture model.

6. The method of claim 1, further comprising in addition to said anatomical features at least one of: roots, crowns, maxillae, mandibles and nerve canals.

7. The method of claim 1, wherein said teeth are segmented individually after said teeth are segmented collectively.

8. The method of claim 1, wherein said individual tooth data files of individual teeth are merged into a total tooth volume representation that includes the total tooth volume data file.

9. The method of claim 1, wherein the sequence of automated segmentation further comprises extracting features of interest from the segmented teeth data file.

* * * * *